US011458096B2

(12) United States Patent
Devraj et al.

(10) Patent No.: US 11,458,096 B2
(45) Date of Patent: Oct. 4, 2022

(54) COMPOSITION AND METHOD OF PRODUCING NANOFORMULATION OF WATER INSOLUBLE BIOACTIVES IN AQUEOUS BASE

(71) Applicant: NANOCEUTICA LABORATORIES PVT. LTD, Hyderabad (IN)

(72) Inventors: Rambhau Devraj, Hyderabad (IN); Pranati Chhatoi, Hyderabad (IN); Naga Hemanth Kumar Parvathabhatla, Hyderabad (IN); Anand Vasant Deshmukh, Hyderabad (IN); Krishna Kaushik Chintabhatla, Hyderabad (IN)

(73) Assignee: PULSE PHARMACEUTICALS PVT. LTD., Telangana (IN)

( * ) Notice: Subject to any disclaimer, the term of this patent is extended or adjusted under 35 U.S.C. 154(b) by 0 days.

(21) Appl. No.: 15/302,495

(22) PCT Filed: Apr. 8, 2015

(86) PCT No.: PCT/IB2015/052541

§ 371 (c)(1),
(2) Date: Oct. 7, 2016

(87) PCT Pub. No.: WO2015/155703

PCT Pub. Date: Oct. 15, 2015

(65) Prior Publication Data

US 2018/0177723 A1 Jun. 28, 2018

(30) Foreign Application Priority Data

Apr. 9, 2014 (IN) ........................... 1872/CHE/2014

(51) Int. Cl.

| | |
|---|---|
| ***A61K 9/107*** | (2006.01) |
| ***A61K 31/122*** | (2006.01) |
| ***A61K 31/192*** | (2006.01) |
| ***A61K 31/202*** | (2006.01) |
| ***A61K 31/593*** | (2006.01) |
| ***A61K 47/10*** | (2017.01) |
| ***A61K 47/12*** | (2006.01) |
| ***A61K 47/18*** | (2017.01) |
| ***A61K 47/24*** | (2006.01) |
| ***A61K 47/26*** | (2006.01) |
| ***A61K 47/32*** | (2006.01) |
| ***A61K 47/34*** | (2017.01) |
| ***A61K 47/44*** | (2017.01) |

(52) U.S. Cl.

CPC .......... *A61K 9/1075* (2013.01); *A61K 31/122* (2013.01); *A61K 31/192* (2013.01); *A61K 31/202* (2013.01); *A61K 31/593* (2013.01); *A61K 47/10* (2013.01); *A61K 47/12* (2013.01); *A61K 47/183* (2013.01); *A61K 47/24* (2013.01); *A61K 47/26* (2013.01); *A61K 47/32* (2013.01); *A61K 47/34* (2013.01); *A61K 47/44* (2013.01)

(58) Field of Classification Search

CPC .. A61K 31/122; A61K 31/192; A61K 31/202; A61K 31/593; A61K 47/10; A61K 47/12; A61K 47/183; A61K 47/24; A61K 47/26; A61K 47/32; A61K 47/34; A61K 47/44; A61K 9/1075

See application file for complete search history.

(56) References Cited

U.S. PATENT DOCUMENTS

| | | | |
|---|---|---|---|
| 5,444,041 | A | 8/1995 | Owen et al. |
| 5,518,738 | A | 5/1996 | Eickhoff et al. |
| 5,994,414 | A | 11/1999 | Franco |
| 6,264,986 | B1 | 7/2001 | Hahnlein et al. |
| 8,318,181 | B2 | 11/2012 | Edelson |
| 8,628,690 | B2 | 1/2014 | Mora-Gutierrez |
| 9,267,050 | B2 | 2/2016 | Heiskanen et al. |
| 9,517,202 | B2 * | 12/2016 | Chen .................... A61K 9/0019 |

(Continued)

FOREIGN PATENT DOCUMENTS

| | | | |
|---|---|---|---|
| EP | 1 597 973 | A1 | 11/2005 |
| EP | 2120872 | B1 | 7/2008 |

(Continued)

OTHER PUBLICATIONS

Bouyer, et al., "Proteins, polysaccharides, and their complexes used as stabilizers for emulsions: Alternatives to synthetic surfactants in the pharmaceutical field?", International Journal of Pharmaceutics, 436 (2012) 359-378, 21 pp.

Written Statement and Evidence, Opposition Under Section 25(2) Against Patent No. 311468, for Composition and Method of Producing Nanoformulation of Water Insoluble Bioactives in Aqueous Base, Patentee: Pulse Pharmaceuticals Pvt. Ltd., Opponent: Tirupati Medicare Limited, dated Jun. 1, 2020, 626 pp.

A.T. Florence and J.A. Rogers, Emulsion stabilization by non-ionic surfactants: experiment and theory, School of Pharmaceutical Sciences, University of Strathclyde, Glasgow, U.K., J. Pharm., 1971, 23, 53-169, 17 pp.

(Continued)

*Primary Examiner* — Jeffrey T. Palenik
(74) *Attorney, Agent, or Firm* — Crowell & Moring LLP

(57) ABSTRACT

Exemplary embodiment of the present disclosure are directed towards a stable nanodispersion comprising an aqueous dispersion medium, a dispersed phase, a surface active agent and optionally, an additive, wherein the aqueous dispersion medium comprises of a nanodispersion stabilizing vehicle base component, wherein the nanodispersion stabilizing vehicle base component improves long term physical stability of the nanodispersion with or without particle size reduction, wherein the dispersed phase comprises of a bioactive compound and wherein the bioactive compound is a lipophilic and hydrophobic. Another exemplary embodiment of the present disclosure is directed towards a method of preparation of such stable nanodispersion.

21 Claims, 6 Drawing Sheets

(56) References Cited

U.S. PATENT DOCUMENTS

| | | | | |
|---|---|---|---|---|
| 2004/0152612 | A1* | 8/2004 | Supersaxo | A61K 9/1075 510/407 |
| 2006/0051462 | A1* | 3/2006 | Wang | A61K 31/122 426/72 |
| 2010/0158998 | A1 | 6/2010 | Fox et al. | |
| 2010/0303827 | A1* | 12/2010 | Sharma, Sr. | A61K 39/39591 424/158.1 |
| 2010/0305218 | A1* | 12/2010 | Wooster | C11C 1/002 426/238 |
| 2011/0229516 | A1* | 9/2011 | Ochomogo | A61K 39/00 424/234.1 |
| 2011/0229554 | A1* | 9/2011 | Narain | A61K 9/0019 424/450 |
| 2011/0294900 | A1 | 12/2011 | Kohli | |
| 2012/0141531 | A1* | 6/2012 | Coulter | A61K 9/107 424/236.1 |
| 2014/0004186 | A1 | 1/2014 | Hustvedt | |

FOREIGN PATENT DOCUMENTS

| | | | |
|---|---|---|---|
| WO | 9420072 | | 9/1994 |
| WO | 97/10814 | | 3/1997 |
| WO | 03/077882 | A2 | 9/2003 |
| WO | 03/105804 | A1 | 12/2003 |
| WO | WO/2007/103294 | A3 | 9/2007 |
| WO | WO2008/077641 | A1 | 7/2008 |
| WO | WO/2009/067734 | A1 | 6/2009 |
| WO | WO/2010/119319 | A1 | 10/2010 |
| WO | 2010/146606 | A1 | 12/2010 |
| WO | WO/2011/075623 | A1 | 6/2011 |
| WO | WO/2013/008083 | A1 | 1/2013 |
| WO | 2013/062424 | A1 | 5/2013 |
| WO | WO/2013/135759 | A1 | 9/2013 |

OTHER PUBLICATIONS

Raman K. Marwaha et al., A randomised controlled trial comparing the efficacy of micellised and fat-soluble vitamin $D_3$ supplementation in healthy adults, British Journal of Nutrition, © The Authors 2019, doi: 10.1017/S0007114518003215, downloaded from https://www. cambridge.org/core..University of Florida, on Mar. 22, 2019 at 16:36:59, 17 pp.

* cited by examiner

Figure 1: Effect of concentration of mono and disaccharide NSVBC on particle size of Nanodispersions containing Vitamin D3
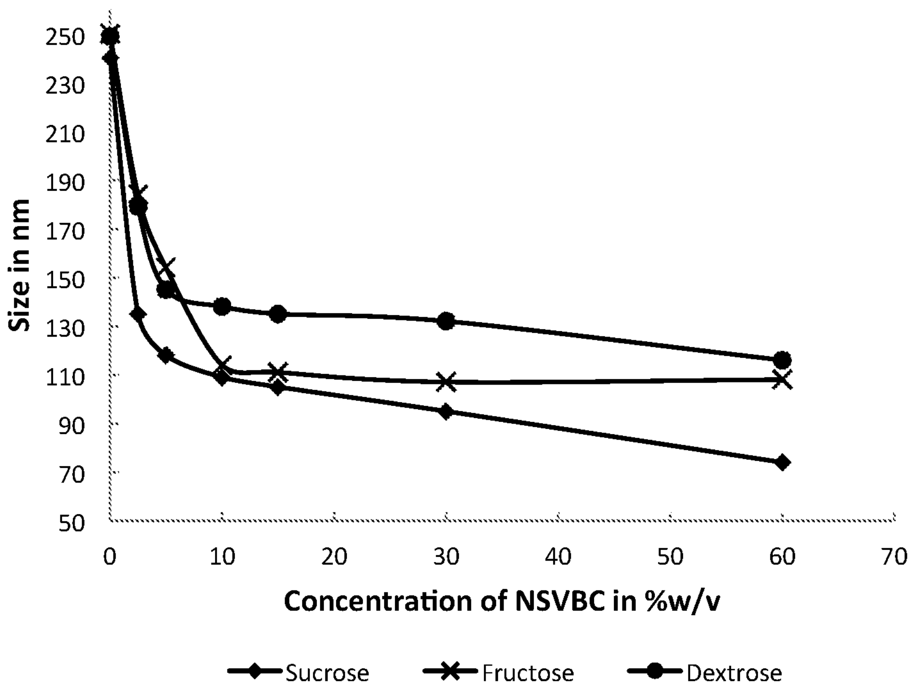
Figure 2: Effect of concentration of Lycasin and Natural Honey NSVBC on particle size of Nanodispersions containing Vitamin D3
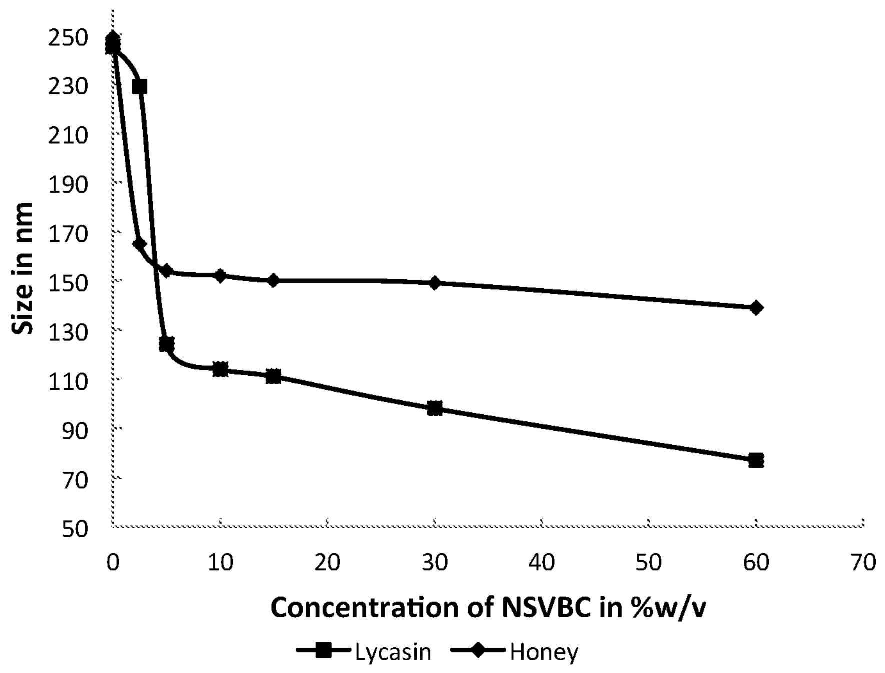

Figure 3: Effect of concentration of polyol NSVBC on particle size of Nanodispersions containing Vitamin D3
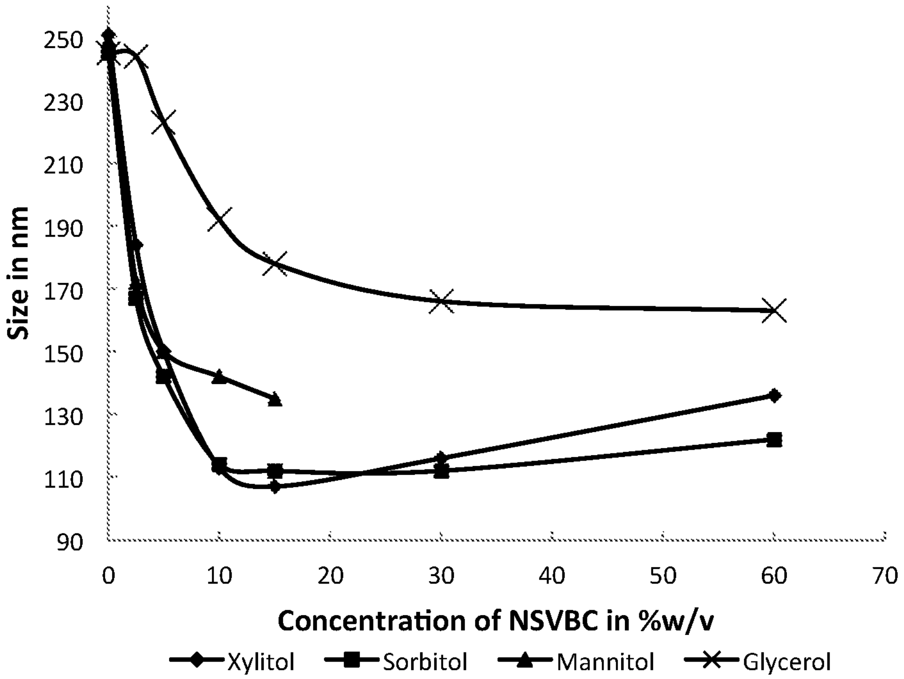
Figure 4: Effect of concentration of Glycol NSVBC on particle size of Nanodispersions containing Vitamin D3
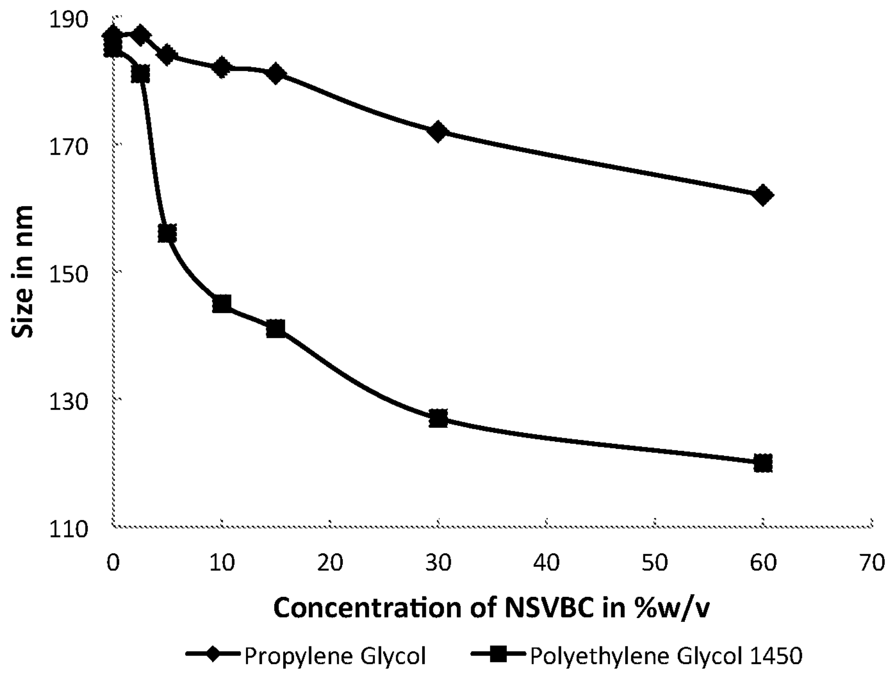

Figure 5: Effect of concentration of NSVBC components on size of Nanodispersion obtained from self emulsifying composition.
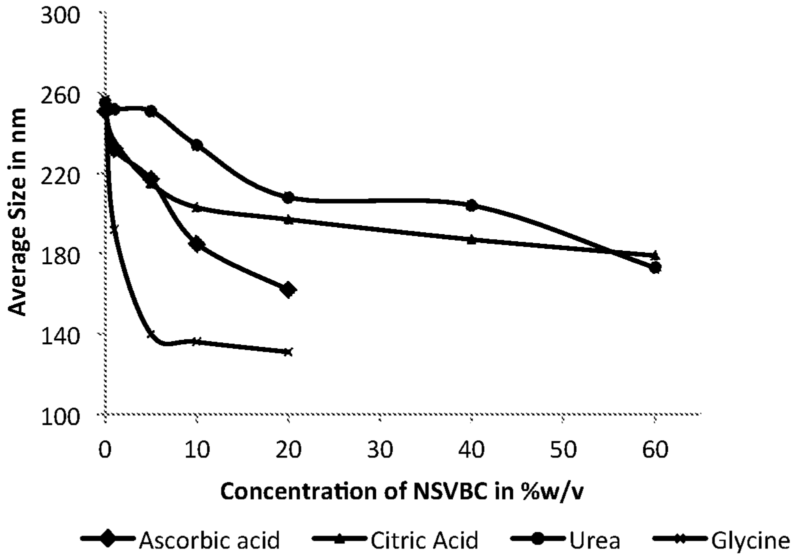
Figure 6: Effect of NSVBC (Scurose62%w/v+Glycerol 5%w/v) on Long-term size stability (at 25°C/60%RH) of nanodispersions obtained from self emulsifying composition
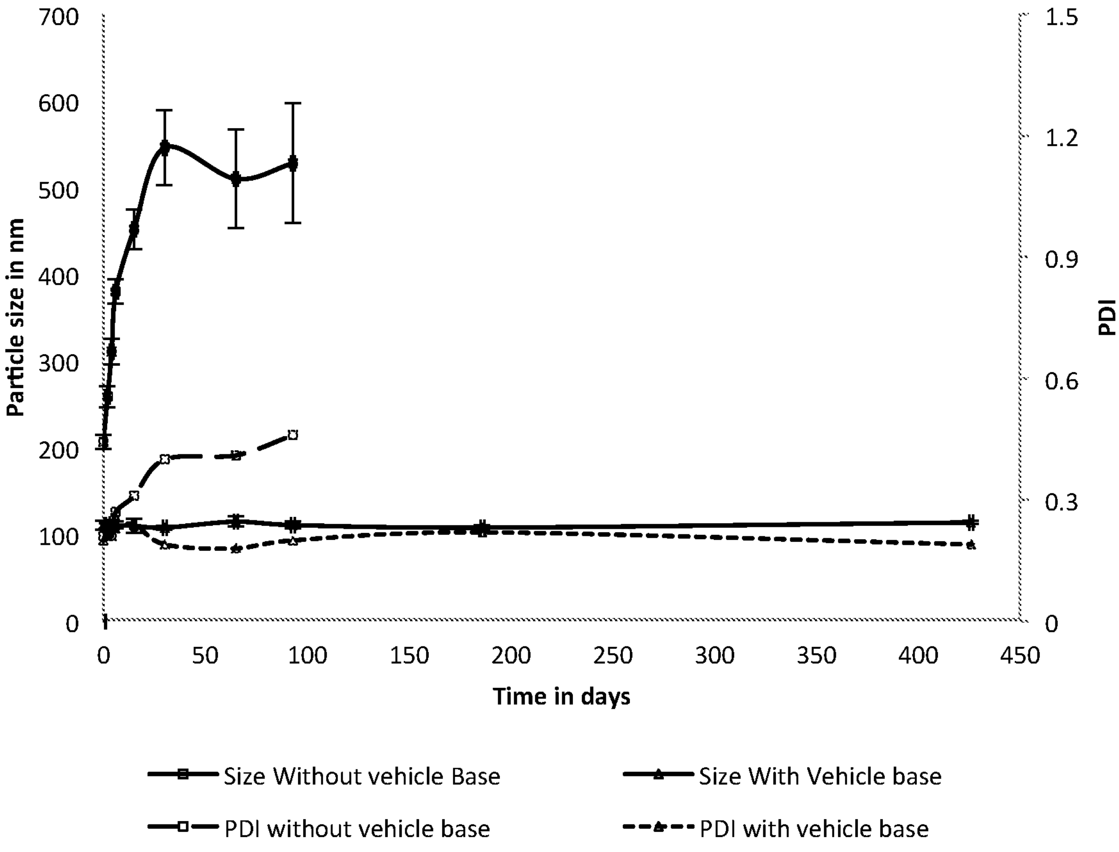

Figure 7: Effect of NSVBC(Scurose50%w/v+Glycerol 5%w/v) on Long-term size stability (at RT) of nanodispersions obtained from self emulsifying composition
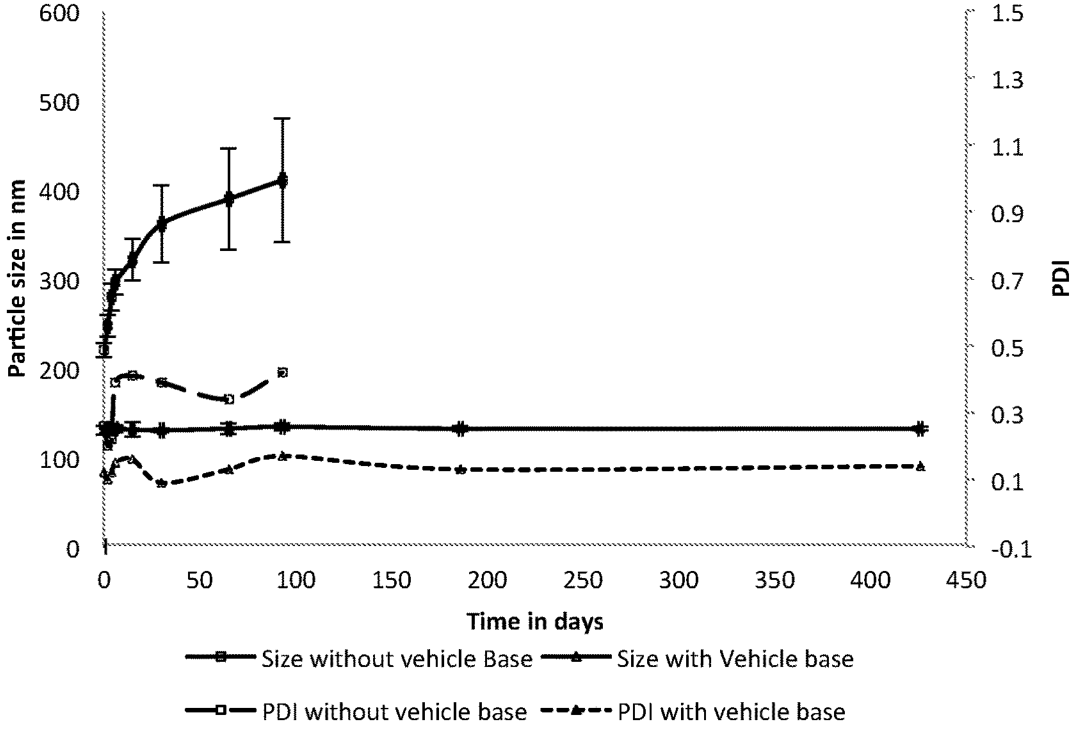
Figure 8: Effect of NSVBC (Scurose40%w/v+Dextrose 15%w/v+Glycerol 5%w/v) on Long-term size stability (at RT) of nanodispersions obtained from self emulsifying composition
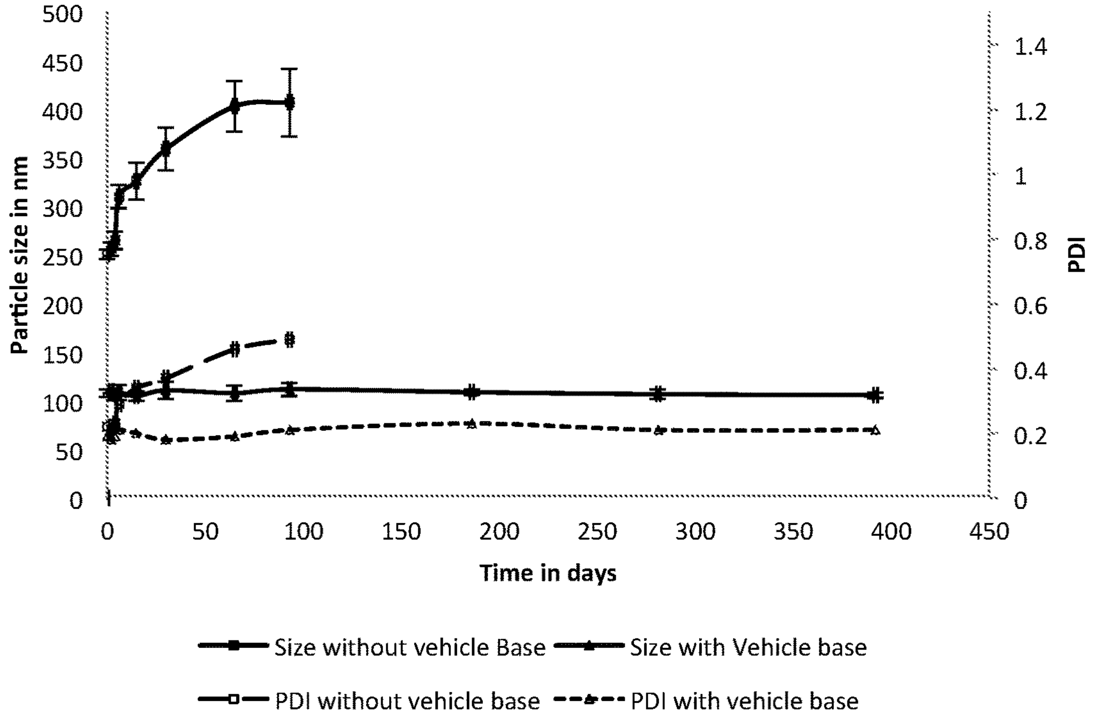

Figure 9: Effect of NSVBC (Lycasin™ 80/55 40%w/v+Fructose 9%w/v +Glycerol 10%w/v) on Long-term size stability (at RT) of nanodispersions obtained from self emulsifying composition
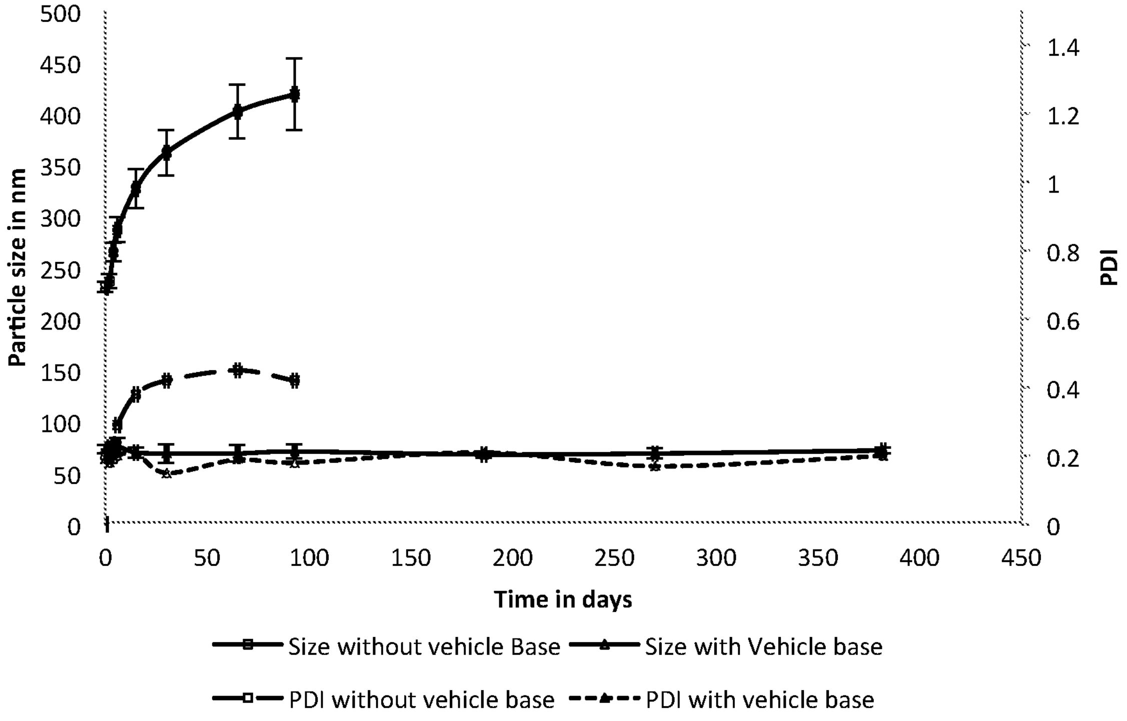
Figure 10: Effect of NSVBC (Lycasin™ 80/55 47%w/v+Glycerol 10%w/v) on Long-term size stability (at RT) of nanodispersions obtained from self
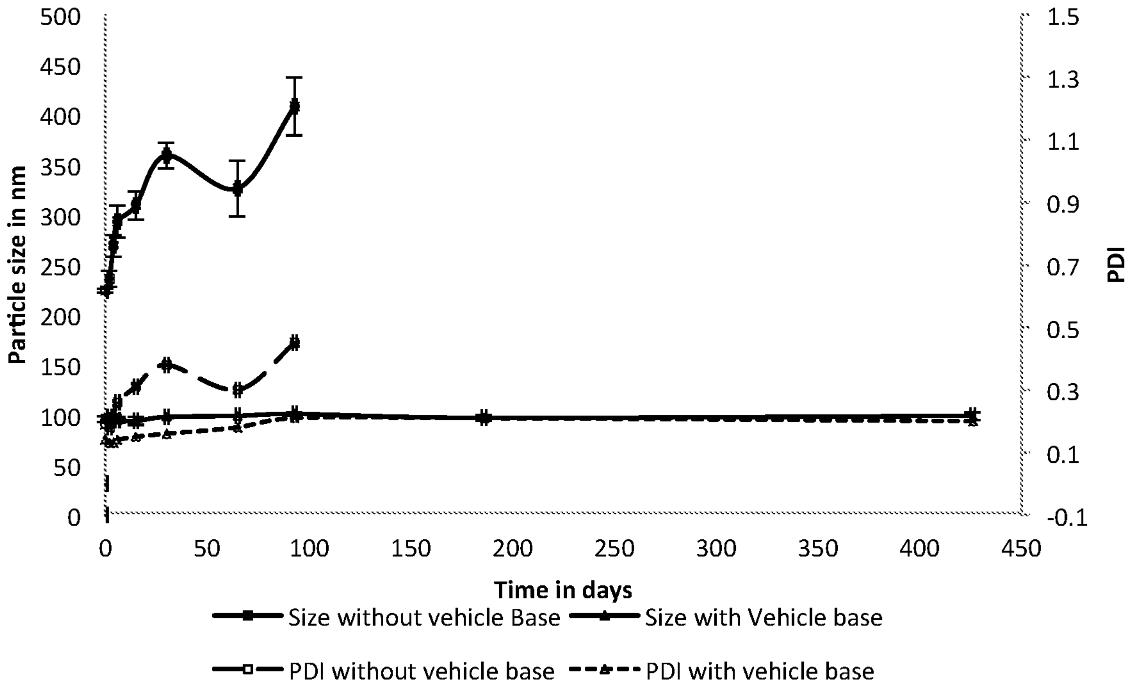

Figure 11: Effect of NSVBC (Scurose30%w/v+Dextrose25% w/v+Fructose5%w/v +Glycerol 5%w/v) on Long-term size stability (at RT) of nanodispersion obtained from self emulsifying composition
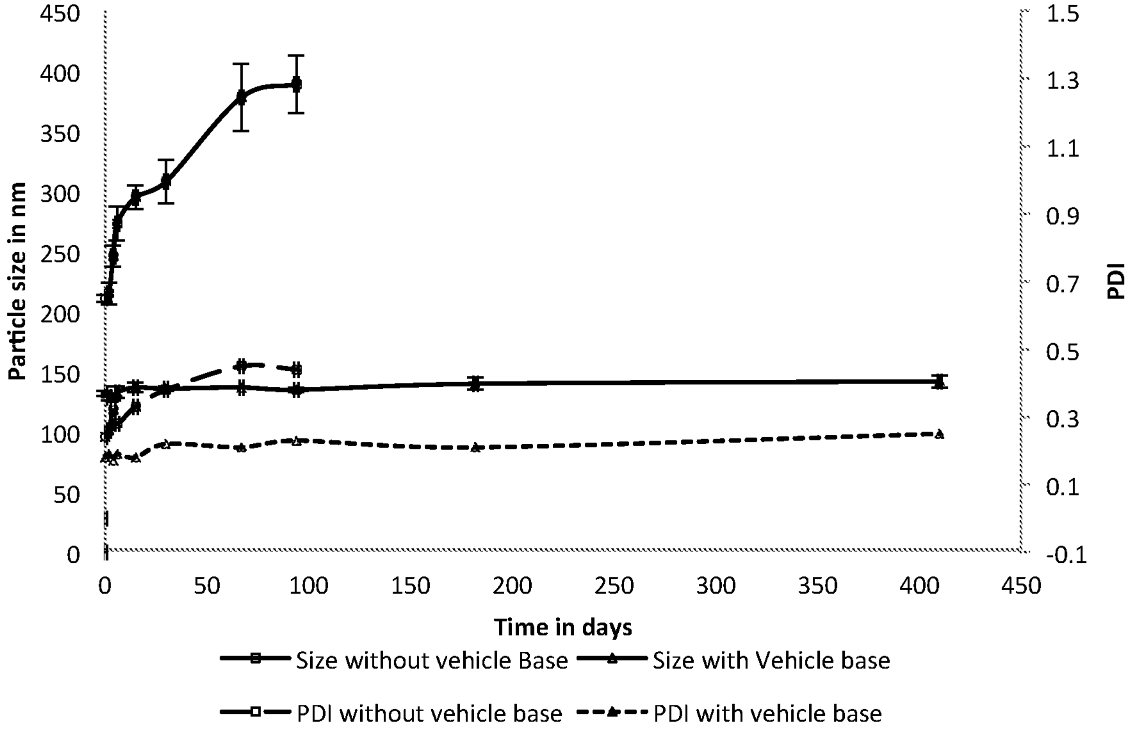

COMPOSITION AND METHOD OF PRODUCING NANOFORMULATION OF WATER INSOLUBLE BIOACTIVES IN AQUEOUS BASE

CROSS-REFERENCE TO RELATED APPLICATIONS

This application is a U.S. National Phase entry under 35 U.S.C. § 371 of International Application No. PCT/IB2015/052541, filed Apr. 8, 2015, which claims the benefit of Indian Patent Application No. 1872/CHE/2014, filed Apr. 9, 2014, the contents of each of which are incorporated herein by reference in their entireties.

TECHNICAL FIELD

The present disclosure generally relates to the field of pharmaceutical nanoformulations. More particularly, the present disclosure relates to a stable nanodispersion comprising an aqueous dispersion medium, a bioactive compound dispersed in a dispersed phase, a surface active agent and a nanodispersion stabilizing vehicle base component and a method of preparing the stable nanodispersion with improved long term physical stability with or without particle size reduction.

BACKGROUND

Nanodispersion also known as submicron dispersions serve as vehicles for the delivery of lipophilic, hydrophobic or water insoluble pharmaceutical ingredients and as well as other bio actives. Nanodispersion have shown to address some of the problems associated with conventional drug delivery systems such as low bioavailability and inconsistent bioavailability.

Although several advantages of nanodispersion have been cited in the literature, developing nanodispersion with optimal particle size, narrow particle size distribution, high drug entrapment in dispersed phase is an outstanding new challenge the formulator has to encounter. The change in physical stability of drug entrapped nanodispersions brings about a change in biological performance of a drug product. Besides this dispersions as such are thermodynamically unstable systems, hence the final acceptance of a nanodispersion depends on its long term stability, appearance and maintenance of it properties and functional characters for a long term under recommended storage conditions.

The ultimate cause of instability is found at particle/liquid interface and the chief parameter against which it is measured is time. The well-known symptoms of instability are: aggregation/flocculation of dispersed phase particles leading to sedimentation which in turn leads to aggregation. Such a flocculation or aggregation leads to particle growth and crystallization when interfacial barriers are weakened. Finally, the gross symptoms of instability manifests as precipitation in solid/liquid and phase separation in liquid/liquid dispersions.

Despite the plethora of scientific theories explaining the mechanisms of instability in dispersed systems, even today formulating an optimally stabilized dispersion system is the most difficult task faced by pharmaceutical formulators.

Primarily, a nano drug delivery vehicle is nanodispersion. The aqueous nanodispersion are converted to solid forms using microencapsulation techniques with the help of freeze or spray drying and other techniques. This attempt is clearly because of instability problems being inherent with liquid nanodispersion. Thus, formulating a liquid nanodispersion with optimal size, and drug entrapment in dispersed phase with long term stability is a challenge.

To obtain the optimum particle size reduction and stability of nano particles during formation, formulators use suitable surface active agents which can preferentially orient/adsorb on dispersed phase particles. Long term stability of disperse systems will be obtained if the interfacial barriers due to surface active agents do not desorbs during the process of ageing. There are several surface active agents available in the categories of ionic, non-ionic and naturally occurring agents. Among them, non-ionic surface active agents are popular because of their low c.m.c (critical micelle concentration) value and variable HLB. Thus, the size reduction and long term stability of the dispersion system is dependent on the performance of such stabilizing ingredients and high energy addition methods used for their processing. However, in many cases having used large concentrations of surface active agents and high energy input processes, the system with a specified size and optimal long term stability may not be obtained. Further, uses of large concentrations of surface active agents are prohibited because of toxicity issues.

Few patents pertaining to nano emulsions, developed liquid oral formulations for the delivery of lipophilic & water insoluble bioactive compounds are reported. These patents used energy addition methods using high pressure homogenization (U.S. Pat. No. 8,628,690, WO2013135759A1, U.S. Pat. No. 8,318,181B2, U.S. Pat. No. 5,994,414A, WO/2007/103294) ultra-sonication, micro fluidization etc. for generation of nano system. Besides High energy input techniques some inventions in the prior art have used spontaneous emulsification methods using water miscible organic solvents such as ethanol, isopropanol, n-propanol, etc. One such invention is described in EP2120872 which showed a size reduction spontaneously to nano level because of alcohols with carbon chain length 1-3. Use of water miscible alcohols and other solvents like acetone etc. have been reported in the literature. Spontaneous emulsification composition called as self-emulsifying nano systems are also reported in the literature (US20110294900A1, WO2010119319 A1,US20140004186 A1, WO2013008083A1). The invention described in WO2009067734 uses water miscible and immiscible alcohols as per claims 11,12,13,14 and employs energy addition (high pressure homogenization) as per claim no. 20.

Some self-emulsifying systems containing large concentrations of surface active agents upon dispersion in to aqueous dispersion medium show smaller average particle size below 200 nm. However, these are highly unstable. Similarly, surfactant micelles and mixed micelles which are obtained by dissolving or dispersing surfactants in aqueous media also show smaller size. However in such systems the micelles can be destroyed by mere dilution and with the addition of commonly used additives like electrolytes, buffering agents, monovalent salts of preservatives etc.

Excepting SEDDS and micellar systems the prior art uses expensive mechanical energy addition techniques to produce a nanodispersion. However using such methods heavy cost and higher time of production are incurred to attain a reasonably good nano size (below 200 nm). Further such dispersions are prone to physical instability and that the prior art reported in this area do not take into consideration the most important physical stability aspect using a cost effective technology.

In the light of the aforementioned discussion there exists a need for nanodispersion/nanoformulations that have long term physical stability and a simple method for preparing such nanodispersion/nanoformulations for achieving particle size reduction as well as long term physical stability.

Nanodispersion has a dispersed phase in the form of particles (solid or semisolid) or droplets (liquid), and such dispersed phase particles have a size below 1000 nm in general. However for the best pharmaceutical applications the size is below 500 nm or particularly below 200 nm or below 100 nm is required. The dispersed phase particles are distributed into a dispersion medium or vehicle. The normal dispersion medium (vehicle) is water. However a pharmaceutical formulator includes many excipients in to dispersion medium (vehicle). The aqueous dispersion medium (vehicle) with dissolved or dispersed excipient components is designated as 'vehicle base' in the context of this invention.

In nanodispersion formulations many excipients other than the one used for interfacial stabilization (surfactants, emulsifiers etc.) are included in the dispersed phase or dispersion medium (vehicle base) for a specific purpose. The viscosifying agents are used to retard sedimentation in solid/liquid dispersions and creaming in liquid/liquid dispersions, sweetening agents are used to improve the palatability, buffers are used to maintain the pH, crystallization inhibitors are used to avoid crystallization on ageing, colours and flavours are used to improve organoleptic properties. Although viscosifying agents by preventing sedimentation and aggregation can increase shelf life to some extent, they are unable to protect the instability eventually developed at interfaces. Therefore there are several literature reports citing particle growth, aggregation and phase separation even in presence of viscosifying agents. Thus, viscous barriers play a secondary role in the stability of dispersed systems.

From the above discussion it is clear that except surface active agents and some hydrocolloids none of the excipients mentioned above were used in nanodispersions with a purpose of bringing about particle size reduction and imparting long term stability. This is because the people in the art using such technologies have no knowledge and are ignorant about the hidden potential of some of the excipients to modify interfacial barrier effect which is scientifically the pivotal property in monitoring the dispersion stability.

We, in the embodiments of this patent unravel the potential interfacial interaction effects of some of the selected excipients used as vehicle base components, hereinafter referred to as "nanodispersion stabilizing vehicle base component(s)" (NSVBC) or "nanodispersion stabilizer(s)" which can beneficially modulate electrostatic and stearic barrier effects of the known stabilizers thereby imparting substantial physical stability to the nanodispersion.

The present invention discloses a stable nanodispersion comprising an aqueous dispersion medium, a bioactive compound dispersed in a dispersed phase, a surface active agent and a nanodispersion stabilizing vehicle base component and a method of preparing the stable nanodispersion, Such a nanodispersion exhibits long term physical stability with or without particle size reduction.

BRIEF SUMMARY

The following presents a simplified summary of the disclosure in order to provide a basic understanding to the reader. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

The object of the present invention is to overcome the drawbacks of prior art. Another object of the invention is to offer a simple commercially viable and highly economical method and composition to obtain nanodispersion with excellent long term physical stability of more than one year (12 months and above).

Exemplary embodiments of the present disclosure are directed towards a stable nanodispersion comprising an aqueous dispersion medium, a dispersed phase, a surface active agent and optionally, an additive, wherein the aqueous dispersion medium comprises of a nanodispersion stabilizing vehicle base component, wherein the nanodispersion stabilizing vehicle base component improves long term physical stability of a nanodispersion with or without particle size reduction, wherein the dispersed phase comprises of a bioactive compound and wherein the bioactive compound is lipophilic and hydrophobic.

Another exemplary aspect of the subject matter is directed towards a method for preparing a stable nanodispersion comprising: mixing a dispersed phase, a dispersion medium and a surface active agent, wherein the dispersed phase comprises of a bioactive compound and wherein the dispersion medium comprises of a nanodispersion stabilizing vehicle base component, wherein the nanodispersion stabilizing vehicle base component improves long term physical stability of a nanodispersion with or without particle size reduction; and optionally, applying at least one of a heat energy and a mechanical energy to obtain at least one of a self-emulsifying system, an oil-in-water nanoemulsion system, a solid lipid nanodispersion system, a polymeric nanodispersion system and a solid lipid-polymer hybrid nanodispersion system.

Nanodispersion claimed in this invention contains lipophilic, hydrophobic or water insoluble bioactive compounds dissolved or dispersed in dispersed phase particles/droplets.

NSVBC are the key ingredients which upon addition to or processing with the components of nanodispersion bring about improvement in physical stability and reduction of size. They are the compounds which are not surface active but have good water solubility, hydrogen bonding ability, and ability to modify the cloud point temperature of nonionic surface active agents.

The NSVBC claimed in this invention when added to or processed with the various compositions of nanodispersions such as solid lipid nano-particulate system, nanoemulsion-system, Self-emulsifying systems, Self micro emulsifying systems, Self nano emulsifying systems, polymeric nano particulate system, lipid polymer hybrid nano-particulate system, or their combinations yields a nanodispersion with excellent long term physical stability of more than one year (12 months) and reduced particle size.

This invention offers a commercially viable and economical method of obtaining a stable nanodispersion containing bio actives using self-emulsifying systems. This invention describes several methods of producing such nanodispersions using basic components of self-emulsifying systems and the variety of NSVBC and their concentrations. It is first time that a stable nanodispersion with self-emulsifying technique is made possible because of the hidden potential of NSVBC to impart substantial stability with greater particle size reduction.

Many self-emulsifying compositions containing vehicle bases yielded nanodispersions which could withstand harsh accelerated conditions. Surprisingly the particle size of a nanodispersion obtained from such a composition and method was stable for several months (6 months) at all the accelerated conditions described in ICH guidelines for stability testing.

This invention probed into the critical factors such as the type of NSVBC, their combinations, the concentration of NSVBC, the method of addition of NSVBC, the method of processing of NSVBC, the extent of dilution of the primary nanodispersions, the amount of water in the final product solid or liquid phase addition of NSVBC to a nanodispersion composition so as to arrive at the maximum benefits from the point of view of physical stability of nanodispersions.

In this invention the details regarding the composition and processing of variety of nanodispersions with optimal particle size and substantially improved stability are provided in several embodiments. All such nano dispersion systems were evaluated for their stability using valid scientific methods available in the literature. In the embodiments of this patent several examples are cited wherein the actual composition, method of processing, method of evaluation of the systems and methods of stability testing are provided. The results were analysed and conclusions were drawn. Based on such conclusions the great hidden potential of said NSVBC and compositions has been discovered.

Advantages of Present Invention a) The size reduction and the physical stability enhancement obtained by this method imparts several desirable characters to the products such as longer-term physical stability to the product and chemical stability to the bioactive compound encapsulated in nano sized dispersed phase particles/droplets of nanodispersion.

b) In addition to the excellent stability benefits, reduction in size enhances bioavailability and improves the palatability of the product.

c) The simplicity of the technology d) Long term stability of nano dispersions e) Improved absorption of bioactive compounds belonging to BCS class II drugs, which have poor aqueous solubility and thus low bioavailability.

f) Improved palatability and high taste masking effect of liquid products containing nano dispersions.

g) The invention results in platform technology which can be applied to variety of insoluble, lipophilic and hydroplobic bioactive compounds. Such compounds include but not limited to Lipophilic antioxidants, lipophilic vitamins, lipophilic drugs.

BRIEF DESCRIPTION OF DRAWINGS

Other objects and advantages of the present invention will become apparent to those skilled in the art upon reading the following detailed description of the preferred embodiments, in conjunction with the accompanying drawings, wherein like reference numerals have been used to designate like elements, and wherein:

FIG. 1 is a graphic representation showing the effect of concentration of mono and disaccharide NSVBC on particle size of Nanodispersions containing Vitamin D3, in accordance with a particular non limiting exemplary embodiment of the present disclosure.

FIG. 2 is a graphic representation showing the effect of concentration of Lycasin and Natural Honey NSVBC on particle size of Nanodispersions containing Vitamin D3, in accordance with a particular non limiting exemplary embodiment of the present disclosure.

FIG. 3 is a graphic representation showing the effect of concentration of polyol NSVBC on particle size of Nanodispersions containing Vitamin D3,in accordance with a particular non limiting exemplary embodiment of the present disclosure.

FIG. 4 is a graphic representation showing the effect of concentration of Glycol NSVBC on particle size of Nanodispersions containing Vitamin D3,in accordance with a particular non limiting exemplary embodiment of the present disclosure.

FIG. 5 is a graphic representation showing the effect of concentration of NSVBC on size of Nanodispersion obtained from self-emulsifying composition, in accordance with a particular non limiting exemplary embodiment of the present disclosure.

FIG. 6 is a graphic representation showing the effect of NSVBC (Sucrose62% w/v+Glycerol 5% w/v) on Long-term size stability (at 25° C./60% RH) of nanodispersions obtained from self-emulsifying composition, in accordance with a particular non limiting exemplary embodiment of the present disclosure.

FIG. 7 is a graphic representation showing the effect of NSVBC (Sucrose50% w/v+Glycerol 5% w/v) on Long-term size stability (at RT) of nanodispersions obtained from self-emulsifying composition, in accordance with a particular non limiting exemplary embodiment of the present disclosure.

FIG. 8 is a graphic representation showing the effect of NSVBC (Sucrose40% w/v+Dextrose 15% w/v+Glycerol 5% w/v) on Long-term size stability (at RT) of nanodispersions obtained from self-emulsifying composition, in accordance with a particular non limiting exemplary embodiment of the present disclosure.

FIG. 9 is a graphic representation showing the effect of NSVBC (Lycasin™ 80/55 40% w/v+Fructose 9% w/v+ Glycerol 10% w/v) on Long-term size stability (at RT) of nanodispersions obtained from self-emulsifying composition in accordance with a particular non limiting exemplary embodiment of the present disclosure.

FIG. 10 is a graphic representation showing the effect of NSVBC (Lycasin™ 80/55 47% w/v+Glycerol 10% w/v) on Long-term size stability (at RT) of nanodispersions obtained from self-emulsifying composition, in accordance with a particular non limiting exemplary embodiment of the present disclosure.

FIG. 11 is a graphic representation showing the effect of NSVBC (Sucrose30% w/v+Dextrose 25% w/v+Fructose 5% w/v+Glycerol 5% w/v) on Long-term size stability (at RT) of nanodispersions obtained from self-emulsifying composition, in accordance with a particular non limiting exemplary embodiment of the present disclosure.

DETAILED DESCRIPTION

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of “including”, “comprising” or “having” and variations thereof herein is meant to encompass the items listed thereafter and equivalents thereof as well as additional items. The terms “a” and “an” herein do not denote a limitation of quantity, but rather denote the presence of at least one of the referenced item. Further, the use of terms “first”, “second”, and “third”, and the like, herein do not denote any order, quantity, or importance, but rather are used to distinguish one element from another.

According to a non limiting exemplary embodiment of the present disclosure, a stable nanodispersion is disclosed that comprises an aqueous dispersion medium, a dispersed phase, a surface active agent and optionally, an additive, wherein the aqueous dispersion medium comprises of a nanodispersion stabilizing vehicle base component, wherein the nanodispersion stabilizing vehicle base component improves long term physical stability of a nanodispersion with or without particle size reduction, wherein the dispersed phase comprises of a bioactive compound and wherein the bioactive compound is lipophilic and hydrophobic.

In accordance with a non limiting exemplary embodiment of the present disclosure, a method for preparing a stable nanodispersion is disclosed, wherein the method comprises of the following steps of: mixing a dispersed phase, a dispersion medium and a surface active agent, wherein the dispersed phase comprises of a bioactive compound and wherein the dispersion medium comprises of a nanodispersion stabilizing vehicle base component, wherein the nanodispersion stabilizing vehicle base component improves long term physical stability of a nanodispersion with or without particle size reduction; and optionally, applying at least one of a heat energy and a mechanical energy to obtain at least one of a self-emulsifying system, an oil-in-water nanoemulsion system, a solid lipid nanodispersion system, a polymeric nanodispersion system and a solid lipid-polymer hybrid nanodispersion system.

According to a non limiting exemplary embodiment of the present disclosure, a method for preparation of a self-emulsifying nanodispersion system is disclosed that comprises of the following steps of: mixing a bioactive compound in a dispersed phase, a surface active agent and optionally, an additive with a lipid to obtain a nanodispersion concentrate, wherein the bioactive compound is lipophilic and hydrophobic; and preparing a stable nanodispersion by any of the following methods:

Method 1: Mixing the nanodispersion concentrate and a nanodispersion stabilizing vehicle base component followed by adding an aqueous dispersion medium, Method 2: Dispersing the nanodispersion concentrate in water to obtain a primary aqueous nanodispersion followed by adding the primary aqueous nanodispersion to an aqueous solution of a nanodispersion stabilizing vehicle base component, Method 3: Dispersing a nanodispersion concentrate in water to obtain a primary aqueous nanodispersion followed by adding the primary aqueous nanodispersion to a nanodispersion stabilizing vehicle base component, Method 4: Adding the nanodispersion concentrate directly to an aqueous solution of a nanodispersion stabilizing vehicle base component, Method 5: Dispersing the nanodispersion concentrate in water to obtain a primary aqueous nanodispersion followed by diluting the primary aqueous nanodispersion with water and further adding a nanodispersion stabilizing vehicle base component.

Method 6: Dispersing the nanodispersion concentrate in water to obtain a primary aqueous nanodispersion followed by adding an aqueous solution of a nanodispersion stabilizing vehicle base component into the primary aqueous nanodispersion and Method 7: Dispersing the nanodispersion concentrate in water to obtain a primary aqueous nanodispersion, wherein the primary aqueous nanodispersion was allowed to stand for a predetermined time to obtain an interfacial equilibrium followed by adding at least one of a nanodispersion stabilizing vehicle base component and an aqueous solution of a nanodispersion stabilizing vehicle base component.

A dispersion has a dispersed phase in the form of particles (solid/semisolid) or droplets (liquid). Such dispersed phase in the form of particles or droplets is distributed into a dispersion medium to form dispersion. In nanodispersion nanoparticles/nanodroplets are dispersed in a dispersion medium. In aqueous nanodispersion the dispersion medium is water or a water solution of any other water soluble or water dispersible components. Hereinafter, the term “particle” refers to both particles (solid/semisolid) and droplets (liquid).

It is well known that surface active agent is the one which facilitates the formation of smaller particle or droplet size and is the one stabilizes them in dispersions because of its ability to form electrostatic/stearic interfacial barriers. Some hydrocolloids also offer stearic barriers with which they are able to stabilize dispersions.

Despite the availability of plenty of such surface active agents and their novel forms obtaining nanodispersion with a desired particle size and long term stability is the most difficult task that formulators encounter even today.

Nanodispersions are much more delicate than micron dispersions (coarse dispersions) and it is not known whether what we have learnt in the past regarding the dispersion formulation will resolve all the issues of nanodispersion formulation and stabilization. One fact which one derives from the past experience is the use of surface-active agents/their blends or addition of energy or use of both are the only way to reduce the particle size of a nanodispersion product. Attempts were not made earlier to explore the other materials or methods to resolve the issue of desired particle size and long term stability of nanodispersions.

We have discovered novel properties of group of materials called “nanodispersion stabilizing vehicle base components” (NSVBC) having special physico-chemical characteristics to be used in the nanodispersions for particle size reduction and stability. When varied the type, concentration and their combinations and added to or processed with nanodispersion components will bring about greater particle size reduction and long term physical stability (365 days). By using the NSVBC in the nanodispersion as described in this invention the use of energy and the time required for processing can be avoided or significantly reduced to achieve desired particle size reduction and long term stability. However, the combined use of NSVBC and energy addition significantly reduces the cost of production as it economizes the use of energy and time. Further such a method can be applied to economize the production of a nanodispersion wherein a superfine nano product is the goal of the formulation. Such a method is feasible alternative to excessive use of surface active agents which are known to reduce the particle size. Further, large concentrations several surface active agents are toxic.

As used herein the specifications, the term ‘Nanodispersion stabilizing vehicle base component” (NSVBC) refers to any compound which is water soluble or water dispersible, upon its addition to or processing with the components of nanodispersion bring about substantial particle size reduction and long term stability of at least 1 year (365 days). The term “NSVBC” denotes such components in their natural form (solid/liquid) or as their aqueous solutions. The NSVBC are non-surface-active compounds having good water solubility, hydrogen bonding ability and are able to modify cloud point temperature (CPT) of the non-ionic surfactants.

As used herein in the specifications, the term 'nanodispersion' refers solid lipid nanodispersion, nanoemulsion, polymeric nano particulate dispersion, lipid-polymer hybrid nanodispersion, and aqueous dispersions of self-emulsifying system, self-micro emulsifying system, self-nano emulsifying systems. The term "self-emulsifying system" herein after includes self-microemulsifying system as well as self-nano emulsifying system. As used herein in the specifications, the term 'bioactive' refer to any hydrophobic, lipophilic and water insoluble bioactive substances which are useful for pharmaceutical, nutraceutical and cosmoceutical purposes.

The term 'size' or 'particle' size wherever mentioned in the embodiments of this invention refers to the average particle or droplet diameter of the dispersed phase.

The term 'long term physical stability' wherever mentioned in the embodiments of this invention refers to the physical stability of a nanodispersion obtained by incorporation of or processing with NSVBC, wherein the nanodispersion exhibits a minimal change in particle size and no aggregation or flocculation or precipitation or phase separation at room temperature over a period of six to 12 months and above.

From the literature it is obvious that except surface active agents and some hydrocolloids none of the compounds can bring about particle size reduction and or impart long term stability.

The several categories of NSVBC given below are not surface active agents by nature in fact they increase the surface tension when used along with water. However, surprisingly such components bring about particle size reduction and long term stability. The nanodispersions with NSVBC have an average particle size ranging from about 10 nm to about 1000 nm. We believe that the hidden potential of these compounds is due to their beneficial effect to modulate electrostatic and stearic barriers via their ability to interact with such interfacial barriers. The nanodispersion stabilizing vehicle base components claimed in this invention belong to but are not limited to a monosaccharide, a di-saccharide, an oligosaccharide, a polysaccharide, a sugar alcohol, a polyol, a glycol, a readymade syrup, a water soluble organic acid, a urea, a water soluble amino acid, a soluble starch, a water soluble protein and a polymer and their combinations in a suitable proportion.

The monosaccharides comprise of at least one of a triose, a tetrose, a pentose and a hexose, wherein the triose comprises of a glyceraldehyde, wherein the tetrose comprises of at least one of an erythrose and a threose, wherein the hexose consists of at least one of a galactose, a mannose, an altrose, an allose, an altrose, a glucose, a gulose an idose, a talose and a fructose. The di-saccharides comprise of at least one of a sucrose, a lactose, a lactulose, a trehalose, a maltose, a cellobiose, a kojibiose, a nigerose, an isomaltose, a β,β-trehalose, an α,β-trehalose, a sophorose, a laminaribiose, a gentiobiose, a turanose, a maltulose, a palatinose, a gentiobiulose, a mannobiose, a melibiose, a melibiulose, a rutinose, a rutinulose and a xylobiose. The oligosaccharides comprise of at least one of a gentianose, a maltotirose and a raffinose. The polysaccharides comprise of an agar, an agarose, an alginic acid, an amylopectin, an amylose, a chitosan, a cyclodextrin, an alpha-cyclodextrin, a sepharose, a dextran, a dextrin, a ficoll, a glucan, a glycogen, a homopolysaccharide, a hypromellose, an inulin, a mucilage, a natural gum, an oxidized cellulose, a pectin, a polydextrose, a polysaccharide peptide, a pullulan and a sepharose.

The polyols comprise of at least one of a glycerol, a miglitol, a momordol, a natural oil polyol, an arabitol, an erythritol, a fucitol, a galactitol, a hydrogenated starch hydrolysate, an iditol, an isomalt, a lactitol, a maltitol, a mannitol, a mannosulfan, a ribitol, a sorbitol, a threitol, a volemitol and a xylitol. The glycol comprises of at least one of a polyethylene glycol having molecular weight ranging from 200 to 10000, a propylene glycol and an ethylene glycol.

The readymade syrups comprise of at least one of a barley malt syrup, a birch syrup, a brown rice syrup, a chocolate syrup, a fruit syrup, a grape syrup, a grenadine syrup, an inverted sugar syrup, a kithul treacle, a maple syrup, a palm syrup, a sorghum syrup, a squash, a sugar beet syrup, a syrup of maidenhair, a torani, a treacle, a yacon syrup, a honey, a high fructose corn syrup and a liquid glucose.

The water soluble organic acids comprise of at least one of an ascorbic acid, a citric acid, a tartaric acid and a glucuronic acid. The water soluble amino acids comprise of at least one of an arginine, an asparagine, a glutamic acid, a glutamine, a glycine, a histidine, an isoleucine, a leucine, a lysine, a methionine, a phenylalanine, a serine, a threonine, a valine, a cysteic acid, a n-glycylglycine and an ornithine and wherein the water soluble protein comprises of at least one of an albumin, a human serum albumin, and an egg albumin.

The additives that can be used in the stable nanodispersion comprises of at least one of a solvent, a viscosifying agent, a dispersing agent, a stabilizer, a surfactant, a sweetening agent, a preservative, a chelating agent, a colouring agent and a flavouring agent or any other additive that are well known in the art, without limiting the scope of the present disclosure.

The NSVBC also includes any other compound which can be used pharmaceutically and which is a non-surface active, highly water soluble, has the ability to undergo hydrogen bonding and is able to modify the cloud point temperature of a non-ionic surfactant.

The aqueous solutions of above mentioned NSVBC comprising of one or more components can be in the range of 1-85% w/v. However, to obtain the most stable nanodispersions with highly reduced particle size the concentration of NSVBC should be optimally around 25-60% w/v. The nanodispersions with reduced particle size can be obtained using more than 60% w/v aqueous solutions of NSVBC. Even some nanodispersions with reduced size can be obtained using aqueous solutions of NSVBC in concentrations more than 60% w/v and more than 80% w/v, however such dispersions are hazy or become hazy on storage. Thus higher the concentration of NSVBC higher is the risk of instability. Such compositions on exposure to accelerated temperatures more than 40° C. result in decrease in cloud point temperature of the dispersion and rapid particle size increase resulting in to complete deterioration of physical stability.

In any of the embodiments described herein a minimum of 30% w/v of water is necessary along with NSVBC to obtain an optimally stabilized nanodispersion.

The above said NSVBC can be used in combination in the form of solids or their aqueous solutions. Such NSVBC compositions when in specific concentration added to or processed with components of variety of nanodispersions impart very high interfacial stability with or without particle size reduction. Thus these NSVBC can resolve the long term stability issues of variety of nanodispersions presently used in the art. Since most of the dispersion systems are prone to physical instability due to thermodynamic reasons, the use of NSVBC to resolve stability and long-term performance issues by simple means without much of the processing cost is the greatest benefit of this invention. It directly reduces the healthcare cost a majority of which is spent on drug formulations.

In accordance with a particular non limiting exemplary embodiment of the present disclosure, nanoemulsions were obtained using energy addition method with high pressure homogenization. The composition: soybean oil as internal phase (10% w/v), Polysorbate 80 as emulsifier (2% w/v), water as continuous phase (q.s), and various concentrations of sucrose (20% w/v, 40% w/v and 60% w/v) as a NSVBC. With increase in sucrose concentration the appearance of the product turned from opaque to translucent. The average particle size of the emulsion on homogenization without NSVBC was 264 nm with a PDI of 0.11. Inclusion of NSVBC during the high pressure homogenization of the emulsion the particle size of the resultant emulsion was substantially reduced (Table 1), with increase in NSVBC concentration.

According to a non limiting exemplary embodiment of the present disclosure, a nanoemulsion was obtained from the above mentioned composition except polysorbate 80 substituted with phospholipon 90G as emulsifier. The concentration of the emulsifier was 1.5% w/v. Even in these emulsions the NSVBC containing (sucrose 60% w/v) emulsion showed substantial particle size reduction with homogenization. The system without NSVBC had an average particle size 216.3 nm, PDI 0.1, whereas the system with SVBC (60% w/v sucrose) showed a particle size of 151 nm, PDI 0.1 and this system was stable for more than 1 year.

In accordance with a non limiting exemplary embodiment of the present disclosure, the nanodispersion was obtained from self-emulsifying system compositions. The lipophilic/hydrophobic/water insoluble drug was dissolved in lipid phase and other components such as surface active agents, solvents, antioxidants, polymers and any other agents required for a specific functionality were added to the lipid phase and were dissolved with the help of heat and mechanical energy. Likewise, a homogenous liquid composition is obtained. This is termed as nanodispersion concentrate (NDC).

A required amount of NDC is dispersed in water to form a primary aqueous nanodispersion. This was further added to the aqueous solution of NSVBC composition (sucrose 62% w/v). Surprisingly the particle size of the resultant nanodispersion was substantially reduced. The resultant dispersions were exposed to accelerated conditions like storage at elevated temperature. The nano system with NSVBC exhibited almost consistent particle size with minor (size increase not more than 10 nm) changes when stored at 40° C. and −20° C. for 14 months.

The nanodispersion systems using self-emulsifying compositions with NSVBC can be processed in variety of ways to obtain an optimum size reduction and long term stability of a nanodispersion containing bioactive substance loaded in dispersed particle.

Method 1: Mixing NDC and NSVBC and finally adding the dispersion medium (water) to obtain nanodispersion.

Method 2: NDC primarily dispersed in water and finally adding such dispersion to aqueous NSVBC composition.

Method 3: NDC primarily dispersed in water and such dispersion is added to NSVBC.

Method 4: NDC is directly added to an aqueous solution of NSVBC.

Method 5: NDC is suitably diluted (1 to 50 times) with water and into such diluted dispersion NSVBC are added.

Method 6: NDC is suitably diluted (1 to 50 times) with water and such diluted dispersion is mixed with aqueous solution of NSVBC.

Method 7: The primary nanodispersion obtained by diluting NDC with water was allowed to stand for 4 to 24 hours to attain interfacial equilibrium before addition of NSVBC or an aqueous solution of NSVBC.

From the above methods of making nanodispersions (1 to 7) the suitably diluted dispersions when mixed with NSVBC result in the best nanodispersion with maximum size reduction and subsequently long-term physical stability.

Further, the NSVBC used as such or their aqueous solutions can be added to the dispersed phase or dispersion medium of the nanodispersions or to the nanodispersions directly and can be further processed with our without use of energy.

In some embodiments of the present disclosure, the lipophilic vitamin D or vitamin E or Vitamin A or Vitamin K or lipophilic antioxidants like Coenzyme Q10, asthaxanthins, ascorbylpalmitate were dissolved in oleic acid as lipid phase. The lipid phase and polysorbate 80 and polaxamer P188 as surface active agents, propylene glycol and benzyl alcohol as solvents and Butylated hydroxyl toluene as antioxidants were mixed to form a homogenous solution (NDC) with the help of heat and mechanical energy to prepare nanodispersions of the said bioactives or their combinations.

Referring to FIG. 1, it is a graphic representation showing the effect of concentration of mono and disaccharide NSVBC on particle size of Nanodispersions containing Vitamin D3, in accordance with a particular non limiting exemplary embodiment of the present disclosure.

Referring to FIG. 2, it is a graphic representation showing the effect of concentration of Lycasin and Natural Honey NSVBC on particle size of Nanodispersions containing Vitamin D3, in accordance with a particular non limiting exemplary embodiment of the present disclosure.

Referring to FIG. 3, it is a graphic representation showing the effect of concentration of polyol NSVBC on particle size of Nanodispersions containing Vitamin D3,in accordance with a particular non limiting exemplary embodiment of the present disclosure.

Referring to FIG. 4, it is a graphic representation showing the effect of concentration of Glycol NSVBC on particle size of Nanodispersions containing Vitamin D3,in accordance with a particular non limiting exemplary embodiment of the present disclosure.

Referring to FIG. 5, it is a graphic representation showing the effect of concentration of NSVBC on size of Nanodispersion obtained from self-emulsifying composition, in accordance with a particular non limiting exemplary embodiment of the present disclosure.

Referring to FIG. 6, itis a graphic representation showing the effect of NSVBC (Sucrose62% w/v+Glycerol 5% w/v) on Long-term size stability (at 25° C./60% RH) of nanodispersions obtained from self-emulsifying composition, in accordance with a particular non limiting exemplary embodiment of the present disclosure.

Referring to FIG. 7, it is a graphic representation showing the effect of NSVBC (Sucrose50% w/v+Glycerol 5% w/v) on Long-term size stability (at RT) of nanodispersions obtained from self-emulsifying composition, in accordance with a particular non limiting exemplary embodiment of the present disclosure.

Referring to FIG. 8, it is a graphic representation showing the effect of NSVBC (Sucrose40% w/v+Dextrose 15% w/v+Glycerol 5% w/v) on Long-term size stability (at RT) of nanodispersions obtained from self-emulsifying composition, in accordance with a particular non limiting exemplary embodiment of the present disclosure.

Referring to FIG. 9, it is a graphic representation showing the effect of NSVBC (Lycasin™ 80/55 40% w/v+Fructose 9% w/v+Glycerol 10% w/v) on Long-term size stability (at RT) of nanodispersions obtained from self-emulsifying composition in accordance with a particular non limiting exemplary embodiment of the present disclosure.

Referring to FIG. 10, it is a graphic representation showing the effect of NSVBC (Lycasin™ 80/55 47% w/v+Glycerol 10% w/v) on Long-term size stability (at RT) of nanodispersions obtained from self-emulsifying composition, in accordance with a particular non limiting exemplary embodiment of the present disclosure.

Referring to FIG. 11, it is a graphic representation showing the effect of NSVBC (Sucrose30% w/v+Dextrose25% w/v+Fructose5% w/v+Glycerol 5% w/v) on Long-term size stability (at RT) of nanodispersions obtained from self-emulsifying composition, in accordance with a particular non limiting exemplary embodiment of the present disclosure.

In accordance to a particular non limiting exemplary embodiment of the present disclosure, a NDC containing vitamin D3 was diluted 10 times with water to form a primary nanodispersion of average size ranging between 240 nm to 260 nm and was allowed to stand for 18 hours. Such a primary nanodispersion was slowly infused/injected into aqueous solution of different NSVBC. In one embodiment the vitamin D3 containing primary nanodispersion said above was added to variety of aqueous solution of NSVBC. In the said embodiment the concentrations of NSVBC in aqueous solutions were 2.5% w/v, 5% w/v, 10% w/v, 15% w/v, 30% w/v, 40% w/v and 60% w/v. The results are shown in FIGS. 1-5.

In other embodiments pertaining to vitamin D3 nanodispersion, a combination of NSVBC were used. These were:

Sucrose62% w/v+Glycerol 5% w/v (FIG. 6);

Sucrose 50% w/v+Glycerol 5% w/v (FIG. 7);

Sucrose 40% w/v+Dextrose 15% w/v+Glycerol 5% w/v (FIG. 8);

Lycasin™ 80/55 40% w/v+Fructose 9% w/v+Glycerol 10% w/v (FIG. 9)

Lycasin™ 80/55 47% w/v+Glycerol 10% w/v (FIG. 10)

Sucrose 30% w/v+Dextrose 25% w/v+Fructose 5% w/v+Glycerol 5% w/v (FIG. 11).

Lycasin™ comprises of a combination of maltitol and sorbitol. All the NSVBC compositions have significantly reduced the particle size of the nanodispersion and even after storage for 1 year at RT the average particle size of such nanodispersions did not change significantly.

In some embodiments pertaining to nanodispersion obtained from Self emulsifying systems, the water content in the primary aqueous NDC dispersion is in the range of 10-80% w/v. A suitably diluted primary dispersion when added to or processed with NSVBC results in a nanodispersion with higher physical stability. However, the extent of dilution is based on the percent dispersed phase in the primary dispersion and can be selected based on the amount of a bioactive in the dispersed phase and the dose of the bioactive in the final product. The improvement in stability and reduction of particle size can be obtained using a wide range of dispersed phase concentrations, ranging from <1% w/v to 25% w/v. At a critical concentration of NDC, a maximum size reduction is obtained when combined with NSVBC.

In accordance with another non limiting exemplary embodiment of the present disclosure, the nanodispersion is a solid-lipid nanodispersion containing bioactive substances in the matrix of the dispersed phase particles and was prepared using suitable lipidic components, water miscible solvents and a specific NSVBC in the dispersion medium. The nanoparticles were obtained by solvent diffusion technique. Vitamin D3 (30 mg),) and Phospholipon 90G (600 mg) were dissolved in 3 ml of ethanol. The ethanolic solution was injected into water or into 40% w/v or into 60% w/v solutions of sucrose containing 1% w/v of polysorbate 80. The results are shown in Table 2.

According to a non limiting exemplary embodiment of the present disclosure, the nanodispersion is a solid lipid-polymer nanodispersion containing bioactive substances in the lipid-polymer matrix particles was prepared using suitable lipidic components, water miscible solvents, surface active agents and a specific NSVBC in the dispersion medium. The nanoparticles were obtained by solvent diffusion technique. Vitamin D3 (30 mg), Phospholipon 90G (600 mg) and PVP $K_{25}$ (30 mg) were dissolved in 3 ml of ethanol. The ethanolic solution was injected into water or into 2% w/v of aqueous solution of polysorbate 80 or into 40% w/v or into 60% w/v solutions of sucrose containing 2% w/v of polysorbate 80. The effect of NSVBC on particle size of the above described nanodispersion is obvious. With increase in concentration of NSVBC (sucrose) the particle size steadily decreased (Table 3).

In accordance with another non limiting exemplary embodiment of the present disclosure, the nano dispersion is a solid lipid nano particulate system containing lipophilic actives like vitamin A, or vitamin D, or Vitamin E, or vitamin K or co enzyme Q-10 were prepared using phospholipid as dispersed phase. The Phospholipon G (300 mg) and Vitamin D3(60 mg) were dissolved in 3 ml of ethanol. The ethanolic solution of these components was slowly injected into either water, or 30% w/v or 60% w/v of aqueous solutions of sucrose without any surface active agents in the dispersion medium, while the aqueous medium was under stirring. The particle size of resultant nanodispersions was evaluated. Particle size was found to decrease with increase in NSVBC concentration (Table 4).

From the above 4 tables it is evident that the NSVBC have a significant effect on the particle size of solid-liquid and liquid-liquid dispersions. The data described in Table 4 is noteworthy. In these systems there is no hydrophilic surface active agent in the dispersion medium like Polysorbate 80 etc. Even then addition of NSVBC has surprisingly decreased the particle size to a significant extent.

In liquid-liquid dispersions surfactant migration from dispersed phase into bulk phase appears to be the mechanism which is augmented/enhanced by the NSVBC. Surprisingly however such a mechanism will not be operable in solid lipid dispersions. Even then the significant size reduction in solid lipid dispersions due to NSVBC is absolutely a novel observation and which promotes very high stability of such systems. Thus this invention unveils the hidden potential of the NSVBC which reduce the particle size and improve the physical stability of solid-lipid and solid-lipid-polymer nanodispersions. Although some such dispersions containing active substances are described in prior art, their applications were limited because of the paucity of methods available to stabilize such systems for prolonged periods for commercial exploitation. Addition of NSVBC to reduce particle size and improve long term stability of such dispersions is simple and cost effective method to produce such dispersions. Thus paves way for the commercial exploitation of such dispersions.

In accordance with another non limiting exemplary embodiment of the present disclosure, a polymeric nanodispersion of Ibuprofen as bioactive substance was formed by using a co polymer of polyvinyl pyrolidone (Plasdone S630) using Phosphotidyl choline (Phospholipon 90G) as surface active agent. Ibuprofen, Plasdone S630 and surface active agent were dissolved in a water miscible solvent such as ethanol. The ethanolic solution was injected into 1% w/v aqueous solution of polysorbate 80 or into 1% w/v polysorbate 80 solution containing 35% w/v of sucrose. The coarse dispersion thus obtained was further purified by removing ethanol completely using rotary vacuum evaporation technique. The purified nanodispersion is condensed to a volume where the concentration of sucrose became 70% w/v. by removing water at 40° C. using rotary vacuum evaporation technique. The resultant nanodispersion is a transparent product and had a size substantially lower than that of the dispersion without NSVBC. The particle size of the nanodispersion with NSVBC was much smaller (108 nm and PDI 0.2.) compared to the system without NSVBC which was in microns size range with poor particle size distribution. The polymeric nanodispersion containing NSVBC was stable for more than 9 months and the system without NSVBC started precipitating within two weeks.

Further, in some embodiments the polymeric nanodispersions of Acetaminophen and Diclofenac sodium were produced with NSVBC and they were found to be highly stable with a smaller particle size.

Most of the nanodispersions described in the embodiments of this invention were exposed to normal ageing stress to assess the real time stability of the nanodispersions containing NSVBC. Besides particle size several other stability parameters viz: weight/ml, viscosity, pH, and entrapment were tested. All these parameters did not change significantly in nanodispersions containing NSVBC for a period of more than 1 year when compared with dispersions without NSVBC.

The invention is now illustrated by non-limiting examples.

EXAMPLE 1

Nanodispersion from Self Emulsifying Systems

Part A:

| | |
|---|---|
| Cholecalciferol | 0.380 g |
| Benzyl Alcohol | 2.1 g |
| Propylene Glycol | 0.87 g |
| Oleic acid | 0.64 g |
| Tween 80 | 3.15 g |
| Poloxamer P188 | 0.8 g |
| Butylated HydroxyToluene | 0.06 g |

PART B: NSVBC

| | |
|---|---|
| Sucrose | 500 g |
| Glycerol | 50 g |
| Purified Water qs. | 1000 mL |

PART C: Other Excipients

| | |
|---|---|
| Sodium benzoate | 2 g |
| EDTA | 0.05 g |

Method of preparation: In the above composition all the ingredients of part A were dissolved with the help of gentle heat and mechanical energy. The homogenous mixture of all ingredients of part A is termed NDC. 7.92 grams of NDC was slowly injected and dispersed into 72 mL of purified water while the water is continuously agitated. The primary aqueous dispersion thus obtained is then slowly added to the NSVBC composition containing 50% w/v of sucrose solution containing 5% w/v of glycerol. Finally sodium benzoate and EDTA were dissolved in a portion of purified hot water and the solution was cooled to room temperature and then added to the final preparation.

EXAMPLES 2 and 3

The composition and method of preparation of NDC and subsequently the preparation of primary nanodispersion is same as described in example 1. The primary nanodispersions of example 2 and example 3 were added to the aqueous solutions of NSVBC, while such solutions are under low shear mixing.

EXAMPLE 2

NSVBC Composition

Lycasin™ 80/55 50% w/v+Glycerol 5% w/v

EXAMPLE 3

NSVBC Composition

Lycasin™ 80/55 40% w/v+Fructose 9% w/v+Glycerol 10% w/v

The average particle size of primary nanodispersions and their size after addition to NSVBC was measured using Photo Correlation Spectroscopy. (ZetasizerNanoseries ZS90).

Accelerated Stability Testing: The nanodispersion product obtained after addition to NSVBC described in Example 1, 2 and 3 were subjected to accelerated stability conditions as per ICH guidelines. During the storage at these conditions the samples were withdrawn at suitable time intervals up to 6 months. The particle size of the samples were measured and recorded to assess the physical stability of the system. Control nanodispersion without NSVBC was also included in the study. The results are recorded in the Table 5.

EXAMPLE 4

Using the NDC composition and method of preparation described in Example 1, primary nanodispersions were obtained. A defined quantity (8 mL) was added into aqueous solution of NSVBC of different composition and concentrations to obtain 100 mL of final nanodispersion product. The study was designed to assess the size reduction potential of various NSVBC and their concentration. The results are recorded in FIGS. 1, 2, 3, 4, and 5.

EXAMPLE 5

Solid-Lipid Nanodispersions

| | |
|---|---|
| Vitamin D3 | 30 mg |
| Phospholipon 90G | 600 mg |
| Ethanol | 3 ml |
| Polysorbate 80 | 1 g |

NSVBC

| | |
|---|---|
| Sucrose | 0 g or 40 g or 60 g |
| Purified Water q.s. | 100 mL |

The ethanolic solution containing vitamin D3 and Phospholipon 90G was injected into 0% w/v or 40% w/v or 60% w/v solutions of sucrose containing 1% w/v of polysorbate 80. The nanodispersion was obtained by solvent diffusion method. The translucent aqueous dispersion was subjected to size analysis (Table 2).

The Solid-Lipid nanodispersion containing 60% w/v of sucrose as NSVBC was subject to long term physical stability studies. During storage at room temperature the particle size changes in this system were negligible whereas, a nanodispersion without NSVBC showed a rapid growth in particle size.

EXAMPLE 6

Polymeric Nanodispersion

| | |
|---|---|
| Ibuprofen | 400 mg |
| Plasdone S630 | 950 mg |
| Phosphotidyl choline | 50 mg |
| Polysorbate 80 | 1 g |
| Ethanol | 4 mL |

NSVBC

| | |
|---|---|
| Sucrose | 70 g |
| Purified water q.s | 100 mL |

Method of Preparation: Ibuprofen, PlasdoneS630 (60:40 linear random co-polymer of N-Vinyl-2-Pyrrolidone and Vinyl acetate) and the phospholipid emulsifier (phosphotidyl choline 90G) were dissolved in 4 mL ethanol. The ethanolic solution containing above components was injected into the aqueous solution of hydrophilic surfactant polysorbate 80 containing 70% w/v sucrose as NSVBC. The nanodispersion thus obtained is further purified by removing ethanol completely using rotary vacuum evaporation. The resultant Ibuprofen nanodispersion was a translucent product with average particle size of 108 nm and PDI 0.26 and it had long-term stability of more than one year. The dispersion prepared without NSVBC was very coarse in micron size range with a very poor particle size distribution and was not stable even during the preparation. The drug started precipitating from the dispersion prepared without NSVBC.

EXAMPLE 7

Solid Lipid-Polymer Hybrid Nanodispersion

| | |
|---|---|
| Vitamin D3 | 30 mg |
| Phosphotidyl choline | 600 mg |
| PVP $K_{25}$ | 30 mg |
| Polysorbate 80 | 2 g |
| Ethanol | 3 mL |

NSVBC

Sucrose 0 g or 40 g or 60 g

Purified water q.s 100 mL

Method of Preparation: The ethanolic solution containing vitamin D3, Phospholipon 90G and PVP $K_{25}$ was injected into purified water without polysorbate 80 or 0% w/v or 40% w/v or 60% w/v solutions of sucrose containing 2% w/v of polysorbate 80. The nanodispersion was obtained by solvent diffusion method. The translucent aqueous dispersion was subjected to size analysis (Table 3).

EXAMPLE 8

Nanoemulsions

| | |
|---|---|
| Decosahexanoic acid (DHA) | 3 g |
| Co-Q10 | 0.5 g |
| Butylated hydroxytoluene (BHT) | 0.05 g |
| Soybean oil | 6.5 g |
| Polysorbate 80 | 2 g |
| Sodium benzoate | 0.2 g |
| Potassium sorbate | 0.1 g |

NSVBC

| | |
|---|---|
| Sucrose | 0 g or 20 g or 40 g or 60 g |
| Purified water q.s | 100 mL |

Method of Preparation:

DHA, Co-Q10 and BHT were dissolved in soybean oil. Polysorbate 80 was dissolved in water containing various concentration of sucrose (0% w/v, 20% w/v, 40% w/v and 60% w/v) as a NSVBC. The oil phase containing bioactives and the aqueous phase (dispersion medium) containing polysorbate 80 with or without NSVBC were mixed together and emulsified using coarse homogenizer. The coarse emulsion obtained (micron size) was subjected to high pressure homogenization for 6 cycles at 12000 psi. The temperature of the emulsion was maintained at 25° C. throughout the processing using a heat exchange device. The results are shown in the Table 1.

With increase in sucrose concentration the appearance of the product turned from opaque to translucent. The average particle size of the emulsion on homogenization without NSVBC was 264 nm with a PDI of 0.11. Inclusion of NSVBC during the high pressure homogenization of the emulsion the particle size of the resultant emulsion was substantially reduced (Table 1), with increase in NSVBC concentration.

TABLE 1

A nanoemulsion stabilized by polysorbate 80, Effect of vehicle base (sucrose) on emulsion droplet particle size.

| S. No | Concentration of vehicle base (sucrose) in % w/v | Particle size of emulsion droplets in nm | PDI (poly dispersivity index) |
|---|---|---|---|
| 1 | 0 | 264 | 0.12 |
| 2 | 20 | 244 | 0.12 |
| 3 | 40 | 214 | 0.13 |
| 4 | 60 | 199 | 0.05 |

TABLE 2

Effect of vehicle base composition on particle size of solid-lipid nanodispersions.

| | VEHICLE BASE COMPOSITION | | |
|---|---|---|---|
| | 1% aqueous polysorbate 80 | 1% aqueous polysorbate 80 containing 40% w/v sucrose | 1% aqueous polysorbate 80 containing 60% w/v sucrose |
| Size | 477 | 412 | 331 |
| PDI | 0.23 | 0.26 | 0.2 |

TABLE 3

Effect of vehicle base composition on particle size of solid-lipid polymer nanodispersions

| | VEHICLE BASE COMPOSITION | | | |
|---|---|---|---|---|
| | Water | 2% w/v aqueous polysorbate 80 | 2% w/v aqueous polysorbate 80 containing 40% w/v sucrose | 2% w/v aqueous polysorbate 80 containing 60% w/v sucrose |
| Size | 503 | 399 | 350 | 305 |
| PDI | 0.45 | 0.21 | 0.28 | 0.24 |

TABLE 4

Effect of vehicle base composition on particle size of solid-lipid nanodispersions stabilized with Phospholipon 90G.

| | VEHICLE BASE COMPOSITION | | |
|---|---|---|---|
| | Water | 30% W/V sucrose solution | 60% W/V sucrose solution |
| Size | 323 | 282 | 218 |
| PDI | 0.4 | 0.35 | 0.3 |

Table 5: Accelerated stability testing of nanodispersions containing optimized concentration vehicle bases: Changes in average particle size with time at various temperatures and humidity conditions as per ICH guidelines. PS denotes phase.

| | Vehicle Base: Water | | | | | | Vehicle Base: Lycasin ™ 80/55 50% w/v + Glycerol 5% w/v | | | | | |
|---|---|---|---|---|---|---|---|---|---|---|---|---|
| Time | 25° C./60% | | 30° C./75% | | 40° C./75% | | 25° C./60% | | 30° C./75% | | 40° C./75% | |
| in Months | Av. Size | PDI | Av. Size | PDI | Av. Size | PDI | Av. Size | PDI | Av. Size | PDI | Av. Size | PDI |
| 0 | 211 | 0.2 | 211 | 0.2 | 211 | 0.2 | 110 | 0.2 | 110 | 0.2 | 110 | 0.2 |
| 1 | 360 | 0.2 | 365 | 0.2 | 440 | 0.3 | 109 | 0.2 | 107 | 0.1 | 108 | 0.2 |
| 2 | 430 | 0.3 | 442 | 0.3 | 510 | 0.4 | 107 | 0.2 | 107 | 0.2 | 103 | 0.2 |
| 3 | 457 | 0.3 | 471 | 0.4 | PS | PS | 109 | 0.2 | 104 | 0.2 | 103 | 0.2 |
| 6 | PS | PS | PS | PS | PS | PS | 101 | 0.2 | 102 | 0.1 | 108 | 0.2 |

| | Vehicle Base: Lycasin ™ 80/55 40% w/v + Fructose 9% w/v + Glycerol 10% w/v | | | | | | Vehicle Base: Sucrose 50% w/v + Glycerol 5% w/v | | | | | |
|---|---|---|---|---|---|---|---|---|---|---|---|---|
| Time | 25° C./60% | | 30° C./75% | | 40° C./75% | | 25° C./60% | | 30° C./75% | | 40° C./75% | |
| in Months | Av. Size | PDI | Av. Size | PDI | Av. Size | PDI | Av. Size | PDI | Av. Size | PDI | Av. Size | PDI |
| 0 | 72 | 0.2 | 72 | 0.2 | 72 | 0.2 | 101 | 0.1 | 101 | 0.1 | 101 | 0.1 |
| 1 | 72 | 0.2 | 73 | 0.2 | 73 | 0.2 | 101 | 0.1 | 103 | 0.2 | 104 | 0.1 |
| 2 | 72 | 0.2 | 71 | 0.2 | 74 | 0.2 | 102 | 0.1 | 102 | 0.1 | 104 | 0.1 |
| 3 | 74 | 0.2 | 71 | 0.2 | 76 | 0.1 | 102 | 0.1 | 105 | 0.1 | 108 | 0.1 |
| 6 | 73 | 0.2 | 75 | 0.2 | 72 | 0.1 | 103 | 0.1 | 103 | 0.1 | 110 | 0.05 |

Although the present disclosure has been described in terms of certain preferred embodiments and illustrations thereof, other embodiments and modifications to preferred embodiments may be possible that are within the principles and spirit of the invention. The above descriptions and figures are therefore to be regarded as illustrative and not restrictive.

Thus the scope of the present disclosure is defined by the appended claims and includes both combinations and sub combinations of the various features described herein above as well as variations and modifications thereof, which would occur to persons skilled in the art upon reading the foregoing description.

We claim:

1. A stable aqueous nanodispersion comprising:

an aqueous dispersion medium comprising a nanodispersion stabilizer and a minimum concentration of water of 30% w/v of the stable aqueous nanodispersion, wherein the nanodispersion stabilizer comprises at least one or more stabilizer(s) selected from the group consisting of glucose, fructose, sucrose, dextrose, glycerol, mannitol, a maltitol liquid, sorbitol, xylitol, polyethylene glycol, and propylene glycol, at a combined concentration of the at least one or more stabilizer(s) ranging from 15% w/v to 70% w/v of the stable aqueous nanodispersion;

a dispersed phase comprising a bioactive compound, and at least one compound selected from the group consisting of a polar lipid, a non-polar lipid, and a polymer, wherein the bioactive compound is in a solubilized form in the at least one compound; and a surface active agent;

wherein the nanodispersion stabilizer is capable of facilitating size reduction, maintaining particle size for at least 1 month at accelerated storage conditions per International Conference on Hormonisation (ICH) guidelines, and substantially reducing the increase of particle size with time in the aqueous dispersion medium thereby improving the long term physical stability of the stable aqueous nanodispersion as compared with nanodispersions without the nanodispersion stabilizers, and maintaining the physical stability of the stable aqueous nanodispersion for a period of at least one year at room temperature at a combined concentration of the at least one or more stabilizer(s) ranging from 15% w/v to 70% w/v of the stable aqueous nanodispersion;

wherein the bioactive compound is vitamin D; and wherein the polymer is a copolymer of polyvinyl pyrrolidone.

2. The stable aqueous nanodispersion as claimed in claim 1, wherein the dispersed phase has an average particle size ranging from about 10 nm to about 1000 nm.

3. The stable aqueous nanodispersion as claimed in claim 1, wherein the nanodispersion stabilizer comprises sucrose and glycerol.

4. The stable aqueous nanodispersion as claimed in claim 1, wherein the nanodispersion stabilizer comprises glycerol, a maltitol liquid, sorbitol, and fructose.

5. The stable aqueous nanodispersion as claimed in claim 1, wherein the nanodispersion stabilizer comprises sucrose, dextrose, and glycerol.

6. The stable aqueous nanodispersion as claimed in claim 1, wherein the nanodispersion stabilizer comprises a maltitol liquid, sorbitol, and glycerol.

7. The stable aqueous nanodispersion as claimed in claim 1, wherein the nanodispersion stabilizer comprises dextrose, fructose, sucrose, and glycerol.

8. The stable aqueous nanodispersion as claimed in claim 1, the stable aqueous nanodispersion being at least one of a solid lipid nanodispersion system, an oil-in-water nanoemulsion system, a self-nano emulsifying system, a polymeric nanodispersion system, and a polymer lipid hybrid nanodispersion system.

9. The stable aqueous nanodispersion as claimed in claim 1, further comprising an additive selected from the group consisting of at least one of a solvent, a viscosifying agent, a dispersing agent, a sweetening agent, a preservative, a chelating agent, a colouring agent, a flavouring agent, and an antioxidant.

10. The stable aqueous nanodispersion as claimed in claim 1, being an oral nanodispersion formulation.

11. The stable aqueous nanodispersion as claimed in claim 1, wherein a weight ratio of the water and the nanodispersion stabilizer ranges from about 30:70 to about 70:30.

12. The stable aqueous nanodispersion as claimed in claim 1, wherein the at least one compound and the bioactive compound are present in the dispersed phase in a mass:mass ratio of the at least one compound to the bioactive compound of greater than 1:1.

13. A stable aqueous nanodispersion comprising:

an aqueous dispersion medium comprising a nanodispersion stabilizer and a minimum concentration of water of 30% w/v of the stable aqueous nanodispersion, wherein the nanodispersion stabilizer comprises at least one or more stabilizer(s) selected from the group consisting of a monosaccharide, a disaccharide, an oligosaccharide, a polysaccharide, a sugar alcohol, a polyol, and a glycol, at a combined concentration of the at least one or more stabilizer(s) ranging from 15% w/v to 70% w/v of the stable aqueous nanodispersion;

a dispersed phase comprising a lipophilic and hydrophobic bioactive compound, and at least one compound selected from the group consisting of a polar lipid, a non-polar lipid, and a polymer, wherein the lipophilic and hydrophobic bioactive compound is in a solubilized form in the at least one compound in a mass:mass ratio of the at least one compound to the lipophilic and hydrophobic bioactive compound of greater than 1:1; and a surface active agent;

wherein the nanodispersion stabilizer is capable of facilitating particle size reduction, maintaining particle size for at least 1 month at accelerated storage conditions per International Conference on Harmonisation (ICH) guidelines, and substantially reducing the increase of particle size with time in the aqueous dispersion medium thereby improving the long term physical stability of the stable aqueous nanodispersion as compared with nanodispersions without the nanodispersion stabilizers, and maintaining the physical stability of the stable aqueous nanodispersion for a period of at least one year at room temperature at a combined concentration of the at least one stabilizer ranging from 15% w/v to 70% w/v of the stable aqueous nanodispersion; and wherein the polymer is a copolymer of polyvinyl pyrrolidone.

14. A method for preparing a stable nanodispersion comprising:

mixing a dispersed phase, an aqueous dispersion medium, a surface active agent, and optionally, an additive, wherein the dispersed phase comprises a lipophilic and hydrophobic bioactive compound and at least one compound selected from the group consisting of a polar lipid, a non-polar lipid, and a polymer, wherein the lipophilic and hydrophobic bioactive compound is vitamin D, wherein the polymer is a copolymer of polyvinyl pyrrolidone, wherein the lipophilic and hydrophobic bioactive compound is in a solubilized form in the at least one compound in a mass:mass ratio of the at least one compound to the lipophilic and hydrophobic bioactive compound of greater than 1:1, wherein the aqueous dispersion medium comprises a nanodispersion stabilizer, the nanodispersion stabilizer comprising at least one or more stabilizer(s) selected from the group consisting of a monosaccharide, a disaccharide, an oligosaccharide, a polysaccharide, a sugar alcohol, a polyol, and a glycol, wherein the nanodispersion stabilizer, at a combined concentration of the at least one or more stabilizer(s) ranging from 15% to 70% w/v of the stable nanodispersion, improves the long term physical stability of the nanodispersion and facilitates particle size reduction when compared with nanodispersions without the nanodispersion stabilizers, wherein the nanodispersion stabilizers maintain the physical stability of the nanodispersion for a period of at least one year at a concentration ranging from 15% w/v to 70% w/v of the stable aqueous nanodispersion; and, optionally, applying at least one of a heat energy and a mechanical energy to obtain a self-emulsifying system, an oil-in-water nanoemulsion system, a solid lipid nanodispersion system, a polymeric nanodispersion system or a solid lipid-polymer hybrid nanodispersion system.

15. The method as claimed in claim 14, wherein the dispersed phase has an average particle size ranging from about 10 nm to about 1000 nm.

16. The method as claimed in claim 14, wherein the monosaccharide comprises at least one of a galactose, a mannose, a xylose, a glucose, a dextrose, and a fructose, wherein the disaccharide comprises of at least one of a sucrose, a lactose, a trehalose, and a maltose, wherein the polysaccharide comprises at least one of a chitosan, a cyclodextrin, an alpha-cyclodextrin, a dextran, a dextrin, a natural gum, and a pullulan, wherein the polyol comprises at least one of a glycerol, a miglitol, a maltitol liquid, a mannitol, a sorbitol, and a xylitol, and wherein the glycol comprises at least one of a polyethylene glycol having a molecular weight ranging from 200 to 10000, a propylene glycol, and an ethylene glycol.

17. The method as claimed in claim 14, wherein the additive comprises at least one of a solvent, a viscosifying agent, a dispersing agent, a sweetening agent, a preservative, a chelating agent, a colouring agent, a flavouring agent, and an antioxidant.

18. The method as claimed in claim 14, wherein preparation of the self-emulsifying system comprises:

a) Mixing a predetermined quantity of the lipophilic and hydrophobic bioactive compound in the dispersed phase, a predetermined quantity of the surface active agent, and, optionally, a predetermined quantity of the additive with a predetermined quantity of the at least one compound to obtain a nanodispersion concentrate;

b) Preparing the stable nanodispersion by any of the following steps of:

i) Mixing a predetermined quantity of the nanodispersion concentrate in a predetermined quantity of the nanodispersion stabilizer followed by adding a predetermined quantity of the aqueous dispersion medium, ii) Dispersing a predetermined quantity of the nanodispersion concentrate in a predetermined quantity of a water to obtain a primary aqueous nanodispersion followed by adding the primary aqueous nanodispersion to a predetermined quantity of an aqueous solution of the nanodispersion stabilizer, iii) Dispersing a predetermined quantity of the nanodispersion concentrate in a predetermined quantity of water to obtain a primary aqueous nanodispersion followed by adding the primary aqueous nanodispersion to a predetermined quantity of the nanodispersion stabilizer, iv) Adding a predetermined quantity of the nanodispersion concentrate directly to a predetermined quantity of an aqueous solution of the nanodispersion stabilizer, v) Dispersing a predetermined quantity of the nanodispersion concentrate in a predetermined quantity of water to obtain a primary aqueous nanodispersion followed by diluting the primary aqueous nanodispersion with a predetermined quantity of water and further adding a predetermined quantity of the nanodispersion stabilizer, vi) Dispersing a predetermined quantity of the nanodispersion concentrate in a predetermined quantity of water to obtain a primary aqueous nanodispersion followed by adding a predetermined quantity of an aqueous solution of the nanodispersion stabilizer into the primary aqueous nanodispersion, or vii) Dispersing a predetermined quantity of the nanodispersion concentrate in a predetermined quantity of water to obtain a primary aqueous nanodispersion wherein the primary aqueous nanodispersion was allowed to stand for a predetermined time to obtain an interfacial equilibrium followed by adding a predetermined quantity of at least one of the nanodispersion stabilizer and an aqueous solution of the nanodispersion stabilizer.

19. The method as claimed in claim 18, wherein the water in the primary aqueous nanodispersion ranges from about 10% w/v to about 80% w/v.

20. The method as claimed in claim 18, wherein the weight ratio of the water and the nanodispersion stabilizer ranges from about 30:70 to about 70:30.

21. The method as claimed in claim 18, wherein the primary aqueous nanodispersion was allowed to stand from about six hours to about 72 hours to obtain the interfacial equilibrium.

* * * * *